United States Patent [19]
Martin et al.

[11] 4,190,958
[45] Mar. 4, 1980

[54] ENDODONTIC DRILL-FILE

[76] Inventors: Howard Martin, 909 Pershing Dr., Silver Spring, Md. 20907; James P. Norris, 1207 Frederick Rd., Baltimore, Md. 21228

[21] Appl. No.: 870,109

[22] Filed: Jan. 17, 1978

[51] Int. Cl.² ............................................. A61C 5/02
[52] U.S. Cl. .................................... 433/102; 433/165
[58] Field of Search ........................... 32/57, 58, 59, 48

[56] References Cited

U.S. PATENT DOCUMENTS

| | | | |
|---|---|---|---|
| 202,006 | 4/1878 | Donaldson | 32/57 |
| 503,744 | 8/1893 | How | 32/57 |
| 1,402,229 | 1/1922 | Hauptmeyer | 32/57 |
| 2,453,696 | 11/1948 | Brooks | 32/59 |
| 4,019,254 | 4/1977 | Malmin | 32/57 |

FOREIGN PATENT DOCUMENTS

| | | | |
|---|---|---|---|
| 2524105 | 1/1976 | Fed. Rep. of Germany | 32/57 |
| 916197 | 1/1963 | United Kingdom | 32/48 |

OTHER PUBLICATIONS

"Emesco" pamphlet, 9-65.

*Primary Examiner*—Louis G. Mancene
*Assistant Examiner*—John J. Wilson
*Attorney, Agent, or Firm*—Walter G. Finch

[57] ABSTRACT

This invention is an improvement in endodontic drills used by dentists specializing in root canal dentistry. Present endodontic practice in the preparation, cleaning, and shaping of root canals in teeth entails the use of inefficient steel drills. The present invention provides a diamond coated drill and file combined of a design that assures an extremely smooth canal surface to facilitate the cleaning and sealing of the root canal.

6 Claims, 2 Drawing Figures

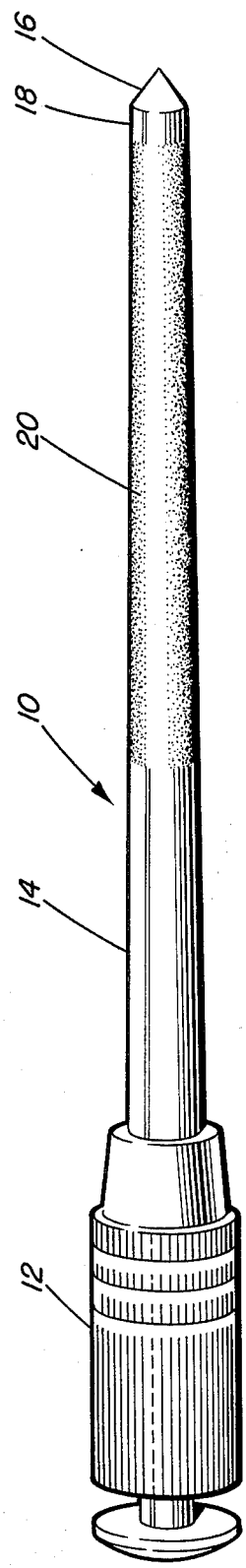
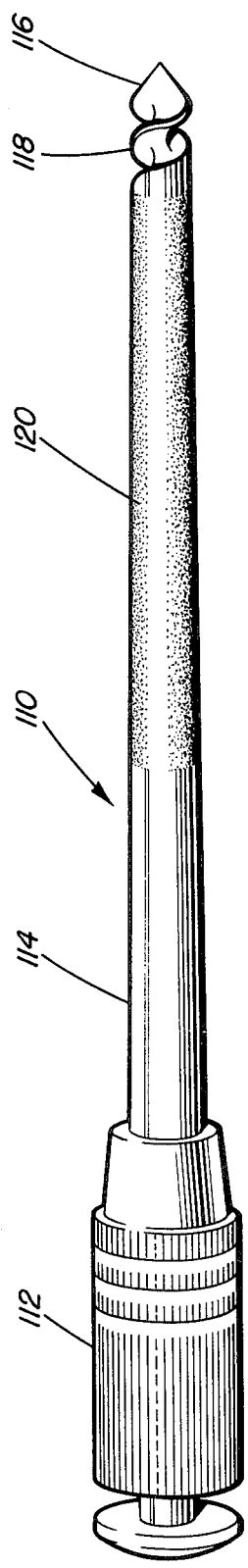
FIG. 1.
FIG. 2.

ENDODONTIC DRILL-FILE

BACKGROUND AND SUMMARY OF THE INVENTION

The invention relates to drills and files and in particular to present drills used in dentistry. More specifically, the invention relates to present endodontic drills used by dentists specializing in root canal dentistry.

The problem involved in root canal dentistry is to provide a properly cleaned and shaped root canal for the work that is to be done. The canals are very narrow and torturous and are difficult to develop and shape to receive a filling material.

At present the method is to use a stainless steel fluted drill. This stainless steel fluted drill is used to clean out the canal, either by manual means by hand, by instrumentation, or by mechanically driven means.

The root canals are normally less than one half of a millimeter in diameter and is filled with soft tissue or dead tissue. The canal is a cylindrically shaped passage from the top portion of the tooth down the bottom of the tooth where the canal exits to the physiological system of the body. The length of the canal will vary with the size of the tooth, normally from about 19 to 23 millimeters in length.

The standard procedure, where root canal work is necessary, is to open the tooth with a regular burr (sometimes spelled bur) type instrument or drill. Then to go into the exposed root canal with either manually operated or mechanically driven stainless steel or tungsten carbide drills.

The operation varies and may be a rotary movement, a quarter turn rotation and also an up and down movement or longitudinal movement. If manually operated, this motion is done by hand.

The present invention provides for diamond-coated endodontic combination drills and files instead of the present fluted instrument. Two types of diamond-coated drill-files are covered by this invention, one has plain tip where the end of the stainless steel shank is not diamond-coated, and the other has special engaging or entry screw or flute on the end that is not diamond-coated.

The basic shank is standard material and may contain 12 to 24 percent chromium and 0.2 percent carbon steel, the actual formula is not part of this invention. The diamond-coated portion may run approximately 10 to 12 millimeters along the file. It should be understood that longer or shorter lengths of diamond coated lengths is within the scope and intent of this invention.

The impregnating or attachment of the diamond-coating may be by adhesives, electrolytically applied, sintered, or by other standard method.

One of the present methods of making a drill is to take a triangular or square shaped shaft and twisting it on itself so that it creates longitudinal spiral flutes. A handle is usually attached at one end for manual operation.

The present endodontic instruments create a lot of rough internal surfaces in which it is difficult to maintain sterility and also difficult to properly seal the canal. Both are very critical to proper root canal dentistry.

The present invention will create a smooth surface area as, in addition to preparing the cylindrical canal, it has a honing action. The smooth interior surface of the prepared cylindrical root canal will then facilitate the cleansing and sterility and the sealing of the canal.

It should be pointed out that other dental drills are very thick and inflexible in relation to the endodontic drill-file of this invention. The drill-file of this invention is very thin and very flexible less than one-half of a millimeter in diameter in order to follow the curve of root canals in a tooth. The file is somewhat conical in shape.

The drill file of the present invention is of a flexible elastic material, having a memory to return to the straight position from the curved position which it must take and is capable to taking, when inserted in a curved root canal. In addition, it must have this memory while rotating in the curved position which transfers the curvature by small increments around the periphery of the drill-file.

The endodontic drill-files of this invention are superior over present drills used, in that present instruments create grooves and rough areas in the wall of the cylindrical-like canal, whereas the present invention using the surface coated with diamond particles provides a honed-like smooth surface. Rough or grooved walls set up conditions that develop voids between the filling material and its interface with the walls of the canal. This can then lead to leakage and eventual failure of the root canal procedure.

It is, therefore, an object of the invention to provide an endodontic drill-file that is flexible to follow the curvature of root canals in human teeth.

It is a further object of the invention to provide an endodontic drill-file that is coated with diamond particles to cut and hone the interior of root canals in human teeth to a very smooth finish.

It is another object of the invention to provide an endodontic drill-file with a plain end for normal endodontic dentistry.

It is still another object of the invention to provide an endodontic drill-file with a fluted end to establish a lead for entering and progressing forward in root canals in human teeth.

It is yet another object of the invention to provide an endodontic drill-file that can be operated manually or be mechanically driven.

Further objects and advantages of the invention will become more apparent in light of the following description of the preferred embodiments.

BRIEF DESCRIPTION OF THE DRAWINGS

FIG. 1 is a pictorial view of an endodontic drill-file with a plain tip;

FIG. 2 is a pictorial view of an endodontic drill-file with a fluted tip.

DESCRIPTION OF THE PREFERRED EMBODIMENTS

Referring to the drawings and particularly to FIG. 1, an improved endodontic drill-file with a plain tip is shown at 10. In FIG. 2 an improved endodontic drill-file with a fluted end is shown at 110.

It is to be noted that illustrated size of the drill-files 10 and 110 in the drawings is many times the size of the actual drill-files which have shafts 14 and 114 respectively of less than one-half millimeter in diameter.

FIG. 1 is one embodiment and FIG. 2 is a second embodiment.

Turning now to FIG. 1, the drill-file 10 has a thin flexible shaft 14 of which a cutting section 20 is coated with diamond particles securely attached to the thin flexible shaft 14. Shaft 14 is slightly tapered toward the plain conical end or tip 16. A short portion of the shaft 14 at the plain conical end or tip 16 may be an uncoated section 18.

Regarding the thin flexible shaft 14 of drill-file 10, it is to be noted that it is of a flexible elastic material having a memory to return to the straight position from the curved position which it must take, and which it is capable of taking, when it is inserted in a curved root canal. In addition, it is to be noted that this drill-file must also have this memory while rotating in the curved position in the curved root canal. This rotation transfers the curvature progressively in small increments around the periphery of the drill-file shaft 14. When withdrawn from the curved root canal the memory within the flexible shaft 14 returns the drill-file 10 to its original straight configuration.

It should be understood that the length of the uncoated section 18 may vary or may be coated the same as the cutting section 20. Such variation is within the scope and intent of this invention.

Likewise it should be noted that the length of the cutting section 20 that is coated with diamond particles may extend along the thin flexible shaft 14 for a greater length than illustrated on the drawing. Such variation is also within the scope and intent of this invention.

The coating of diamond particles on the cutting section 20 makes it possible to not only cut the interior surfaces of the actual root canal of the tooth, but hones the surface to a very smooth finish.

At the end of shaft 14, opposite from the aforementioned conical end or tip 16, the shaft 14 is affixed within a conventional knurled cylindrical head 12 for holding the flexible shaft 14 and arranged to be chucked for a mechanical instrument drive or grasped for manual manipulation. Motion may be either in a rotary direction or in a longitudinal direction. It may also be operated in the reciprocating quarter-turn motion.

The shaft 14, which is normally approximately 25 millimeters long and made of stainless steel, is tapered to provide a diametrical increase of approximately 0.02 millimeter per millimeter of shaft length. The shaft 14 is normally less than 0.5 millimeter at the conical end or tip 16, and increases by the taper to the knurled cylindrical head 12.

The conical end or tip 16, the included angle of which is approximately 75°, has the uncoated section 18 adjacent to it. The uncoated section 18, if uncoated, is approximately one millimeter in length.

The cutting section 20 normally approximately 15 millimeters in length, but as aforementioned may be extended.

The diamond particles applied to the cutting section 20 may be applied electrolytically or by other suitable means.

The present invention permits not only a drilling action, but also a honing action to produce the smooth surface on the inside of the canal. The present invention permits a filing action in addition to the drilling action which is a distinct improvement over present endodontic drills.

The second embodiment shown in FIG. 2 is generally similar to the first embodiment in FIG. 1 and similar teachings of drill-file 10 apply to drill-file 110, except for the conical end or tip 16 and the uncoated section 18 which will be described hereinafter.

Drill-file 110 consists of a tapered shaft 114, a cutting section 120 with a coating of diamond particles, and the shaft 114 secured or held in a knurled cylindrical head 112, all of similar construction and configuration to the comparable structure and configuration of drill-file 10.

At the end of the shaft 114 of drill-file 110, opposite the end where the knurled cylindrical head 112 is located, the shaft 114 is configured into a fluted end 118 that terminates in a pointed end 116. The fluted end 118 and pointed end 116 are not coated with diamond particles.

The fluted end 118 provides a means establishing a lead for entering and progressing forward in a root canal when the tooth structure is such that a plain end, such as conical end or tip 16 on drill-file 10, will not advance easily. The length of the fluted end may vary from approximately two millimeters or longer.

It should be noted that since human teeth vary in size and consequently the actual root canals will vary, the drill-files 10 and 110 may be provided in a range of diameter sizes of 0.10 millimeter to 1.50 millimeter by 0.05 millimeter increments. Such variation is within the scope and intent of this invention.

Accordingly, modifications and variations to which the invention is susceptible may be practiced without departing from the scope and intent of the appended claims.

What is claimed is:

1. An endodontic drill-file, comprising:
a memoried flexible shaft means of very thin configuration, said memoried flexible shaft having a tapered end, said memoried flexible shaft means having a memory which returns said flexible shaft means to an original straight position of configuration from a curved position, said curved position being assumed when inserted in a curved root canal of a human tooth, when said flexible shaft means is removed from said curved root canal, and further, said memory to return said flexible shaft means to an original straight position of configuration being maintained when said flexible shaft means is rotated within said curved root canal of a human tooth and in said curved position, said curved position being assumed when inserted in said curved root canal, said curvature being transferred progressively in small increments around the periphery of said flexible shaft; and
a cutting means on the surface of said flexible shaft means.

2. The endodontic drill-file recited in claim 1 wherein the memoried flexible shaft means is formed of flexible elastic stainless steel and is tapered.

3. The endodontic drill-file recited in claim 2 and additionally, a conical end tip positioned on said tapered end of said flexible shaft means as a lead for said flexible shaft means.

4. The endodontic drill-file recited in claim 2 and additionally, a fluted end tip positioned on said tapered end of said flexible shaft means as an advancing lead for said flexible shaft means.

5. The endodontic drill-file recited in claim 1 wherein the cutting means consists of diamond particles attached to said flexible shaft means.

6. The endodontic drill-file recited in claim 1 and additionally holding means for said flexible shaft means, said holding means being capable of use for manually manipulating said flexible shaft means in a reciprocating rotary, or longitudinal direction and also for use for mechanically driving said flexible shaft means in a reciprocating, rotary as well as longitudinal direction.

* * * * *